(12) United States Patent
Canatella (10) Patent No.: US 10,385,999 B2
(45) Date of Patent: Aug. 20, 2019

(54) FLUID COUPLING DEVICES

(71) Applicant: Terumo Cardiovascular Systems Corporation, Ann Arbor, MI (US)

(72) Inventor: Timothy John Canatella, Jarrettsville, MD (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 878 days.

(21) Appl. No.: 14/795,337

(22) Filed: Jul. 9, 2015

(65) Prior Publication Data

US 2017/0009920 A1   Jan. 12, 2017

(51) Int. Cl.
| F16L 37/098 | (2006.01) |
|---|---|
| A61M 39/10 | (2006.01) |
| A61M 39/26 | (2006.01) |

(52) U.S. Cl.
CPC ...... *F16L 37/0985* (2013.01); *A61M 39/1011* (2013.01); *A61M 39/26* (2013.01); *A61M 2039/1027* (2013.01)

(58) Field of Classification Search
CPC ............... F16L 37/0985; A61M 39/26; A61M 39/1011; A61M 2039/1027
See application file for complete search history.

(56) References Cited

U.S. PATENT DOCUMENTS

| 4,844,512 A * | 7/1989 | Gahwiler ............. F16L 37/084 285/275 |
|---|---|---|
| 4,969,879 A | 11/1990 | Lichte |
| 4,991,882 A * | 2/1991 | Gahwiler ............. F16L 37/084 285/319 |
| 5,104,157 A | 4/1992 | Bahner |
| 5,213,376 A * | 5/1993 | Szabo ................... F16L 37/084 285/39 |
| 5,324,080 A * | 6/1994 | McNaughton ........ F16L 37/084 285/319 |
| 5,425,556 A | 6/1995 | Szabo |
| 5,441,313 A | 8/1995 | Kalahasthy |

(Continued)

FOREIGN PATENT DOCUMENTS

GB        2323418 A   *   9/1998   .......... F16L 37/0985

OTHER PUBLICATIONS

PCT Notification of International Search Report & Written Opinion dated Dec. 2, 2016 in corresponding International Application No. PCT/US2016/41289 (11 pages).

*Primary Examiner* — James M Hewitt, II
(74) *Attorney, Agent, or Firm* — Fish & Richardson P.C.

(57) ABSTRACT

Fluid coupling devices for connecting to and disconnecting from a male barbed fitting to provide a continuous flow path or a flow termination point, include a frame and an elastomeric sealing material disposed about and at least partially encapsulating the frame. The frame can have a first end including a connecting element. The frame can also have a second end including a ring that has two inwardly directed, radial locking tabs. At least a portion of the sealing material can define a thru lumen. At least a portion of the thru lumen can include a tapered, inner portion configured to create a sealed connection with a male barbed fitting. The second end of the fluid coupling device, when compressed, can deflect the locking tabs in a radially outward direction for releasing the male barbed fitting.

22 Claims, 4 Drawing Sheets

(56) References Cited

U.S. PATENT DOCUMENTS

| | | | |
|---|---|---|---|
| 5,462,313 A | 10/1995 | Rea et al. | |
| 5,466,017 A * | 11/1995 | Szabo | F16L 37/0987 |
| | | | 285/319 |
| 5,568,946 A | 10/1996 | Jackowski | |
| 5,609,370 A | 3/1997 | Szabo et al. | |
| 6,371,529 B1 | 4/2002 | Szabo et al. | |
| 7,390,028 B2 | 6/2008 | Blazek | |
| 7,547,048 B2 | 6/2009 | Catlow | |
| 7,618,070 B2 | 11/2009 | Stoll et al. | |
| 2006/0264911 A1 | 11/2006 | Nelson | |
| 2007/0088324 A1 | 4/2007 | Fangrow | |
| 2009/0188575 A1* | 7/2009 | Williams | F16L 37/0985 |
| | | | 137/798 |
| 2010/0063482 A1 | 3/2010 | Mansour et al. | |
| 2011/0298209 A1 | 12/2011 | Nguyen et al. | |
| 2014/0284915 A1 | 9/2014 | Arnold et al. | |

* cited by examiner

FLUID COUPLING DEVICES

TECHNICAL FIELD

This document relates to fluid coupling devices. For example, this document relates to fluid coupling devices for quickly connecting to and disconnecting from a male barbed fitting.

BACKGROUND

Fluid couplers are widely utilized in a variety of industrial, household, medical, hydraulic, pneumatic, and commercial applications. There is a continuing need in the art for fluid couplers that offers convenient device operation, improved coupling security, and simplified device manufacturing.

SUMMARY

This document provides fluid coupling devices. For example, this document provides fluid coupling devices for quickly connecting to and disconnecting from a male barbed fitting to provide a continuous flow path or a flow termination point, as desired.

In one implementation, a fluid coupling device can include a frame that has a first frame portion, a second frame portion, and an elastomeric sealing material. The first frame portion can include a ring and two inwardly directed, radial locking tabs. The second frame portion can include a connecting element. The elastomeric sealing material can be disposed about and at least partially encapsulate the frame. The sealing material can define at least a portion of a lumen that includes at least one sealing surface configured to form a sealed connection with a male barbed fitting. The fluid coupling device, when compressed, can deflect the locking tabs in a radially outward direction for releasing the male barbed fitting.

In some embodiments, the fluid coupling device has a non-compressed state configured for sealably coupling to the male barbed fitting and a compressed state configured for releasing the male barbed fitting. The ring of the frame can have a circular cross-section when the fluid coupling device is in the non-compressed state and an oval cross-section when the fluid coupling device is in the compressed state. In some embodiments, the locking tab can be located 180 degrees apart from one another. In some embodiments, the first frame portion of the frame further can include a deflectable ring configured to increase a radial distance between the locking tabs. In some embodiments, a radial distance between the locking tabs of the fluid coupling device in the compressed state can be larger than a radial distance between the locking tabs of the fluid coupling device in the non-compressed state. In some embodiments, a radial distance between the locking tabs of the fluid coupling device in the compressed state can range from about 10 mm to about 35 mm. In some embodiments, a radial distance between the locking tabs of the fluid coupling device in the non-compressed state can range from about 7 mm to about 30 mm. In some embodiments, a difference of a radial distance between the locking tabs of the fluid coupling device in the compressed and the non-compressed state can range from about 0.5 mm to about 5.0 mm.

In some embodiments, the elastomeric sealing material can include an exterior surface having two press elements. Each press element can include a protruding feature on the exterior surface of the sealing material, as desired. The press elements can optionally be formed on the ring and each press element can include two radially, outwardly extended prongs and a curved depression between the two prongs. In some embodiments, the elastomeric sealing material can include a frustoconical sealing surface encapsulated about the first frame portion. The frustoconical sealing surface can optionally be defined by an angle relative to the longitudinal axis of a body of the device that is complementary to a shape of a male barbed fitting. In some embodiments, an angle of the frustoconical sealing surface relative to the longitudinal axis of a body of the device can range from about 15 degrees to about 40 degrees. In some embodiments, a ratio of a maximum inner diameter to a minimum inner diameter of the frustoconical sealing surface can range from about 1:1 to about 1:10. The elastomeric sealing material can optionally include a cylindrical sealing surface encapsulated about at least a portion of the first frame portion. The cylindrical sealing surface can have an inner diameter ranging from about 5 mm to about 15 mm.

In some embodiments, the connecting element is a barbed tubular member, a luer-lock connector, or a second male barbed fitting connector.

In another implementation, a fluid coupling device can include a body that has a first fitting at a first end and a second fitting at a second end. The first fitting may include a female fitting that has a manually deformable frame and two inwardly directed locking tabs adapted for releasably connecting to a male barbed fluid connector. The body can define a lumen adapted for sealingly mating with the male barbed fluid connector.

In some embodiments, the two inwardly directed locking tabs can be positioned substantially circumferentially opposite each other on the frame. The second fitting can optionally include a male fitting that has a barbed tube configured for insertion in a female type fluid connector.

In yet another implementation, a fluid coupling device can include a frame that includes a manually deformable coupling element. The coupling element can include two inwardly directed locking tabs positioned substantially circumferentially opposite each other on the frame.

Particular embodiments of the subject matter described in this document can be implemented to realize one or more of the following advantages. In some embodiments, the fluid coupling devices provided herein are configured to allow for convenient separation and reconnection of a barbed fitting connection. A typical barbed fitting connection relies on deformation from an interference fit between the male-side barb and the female-side tube. Hence, the typical barbed fitting can be difficult to separate. In addition, the interference fit and the difficult separation process may prevent subsequent reconnection of the typical barbed fitting such that the fitting cannot thereafter operate in a leak-proof and/or sufficiently pressure-resistant fashion. In contrast, in some embodiments the fluid coupling devices provided herein do not rely on deformation from an interference fit. Rather, disconnection of the fluid coupling devices is facilitated by reversibly disengaging the coupling's locking tabs on the female side from the barb on the male side. The fluid coupling device provided herein can be installed, removed and re-used through the use of the locking tabs, or a mechanical interlock feature, that can be engaged and disengaged as a connector. Hence, and as explained further below, the configuration of the fluid coupling devices provided herein allow for convenient disconnection and subsequent reconnection multiple times. Other aspects, features, and advantages will be apparent from the description and drawings, and from the claims.

DESCRIPTION OF DRAWINGS

The accompanying drawings are included to provide a further understanding of the disclosure and are incorporated in and constitute a part of this specification, illustrate embodiments of the disclosure, and together with the description, serve to explain the principles of the disclosure, wherein.

Like reference symbols in the various drawings indicate like elements. It should also be noted that the accompanying drawing figures referred to herein are not all drawn to scale and may be exaggerated to illustrate various aspects of the present disclosure, and in that regard, the drawing figures should not be construed as limiting.

DETAILED DESCRIPTION

Figure 1:
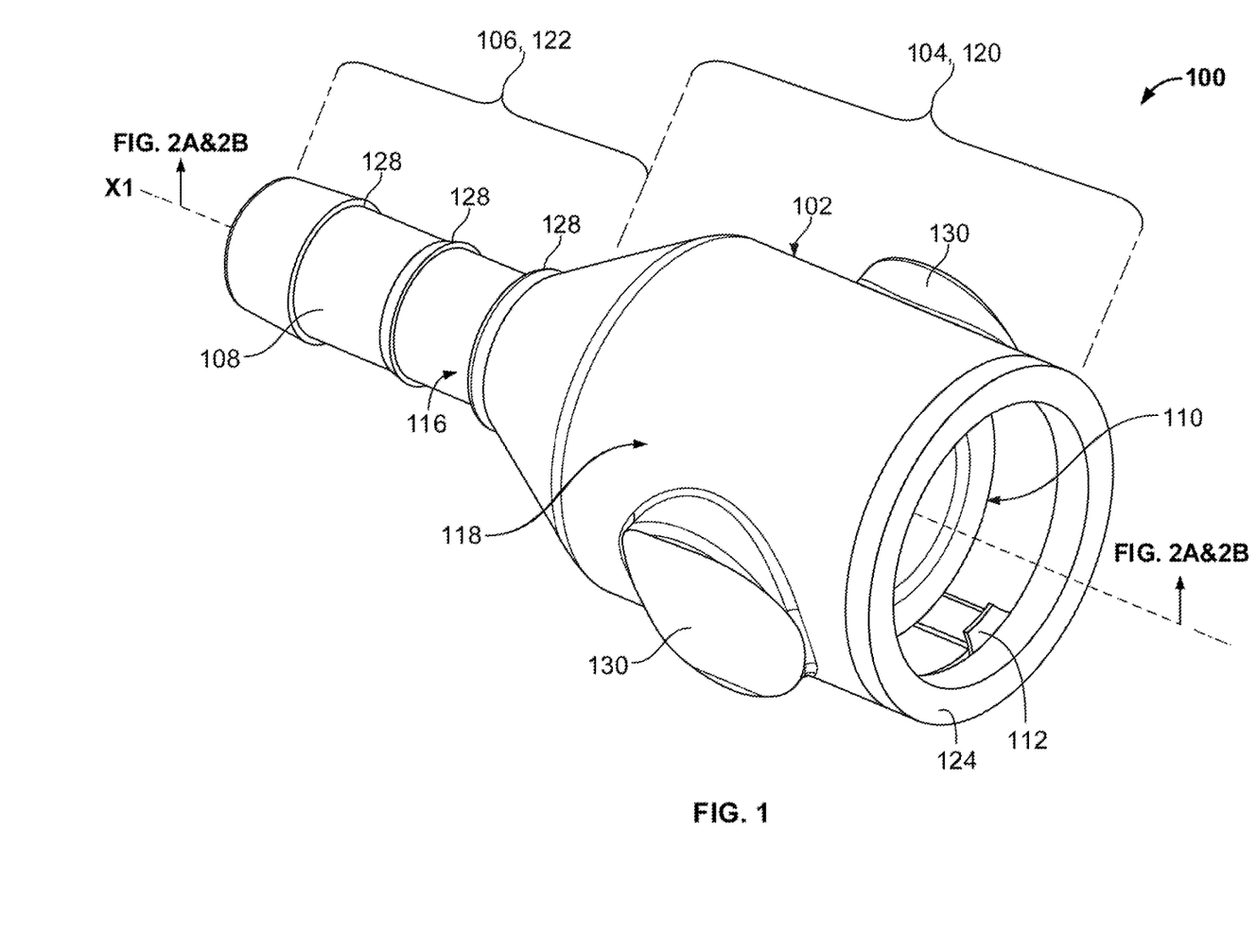
FIG. 1 is a perspective view of an exemplary fluid coupling device.
Figure 2A:
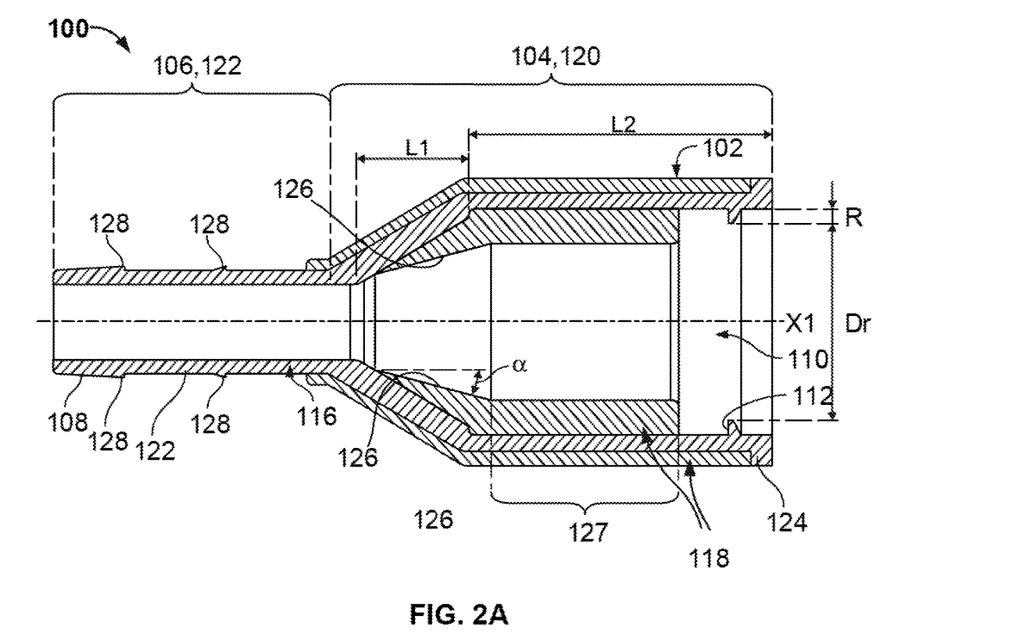
FIGS. 2A and 2B are cross-sectional side views of the fluid coupling device of FIG. 1 without and with a male barbed fitting, respectively.
Figure 2B:
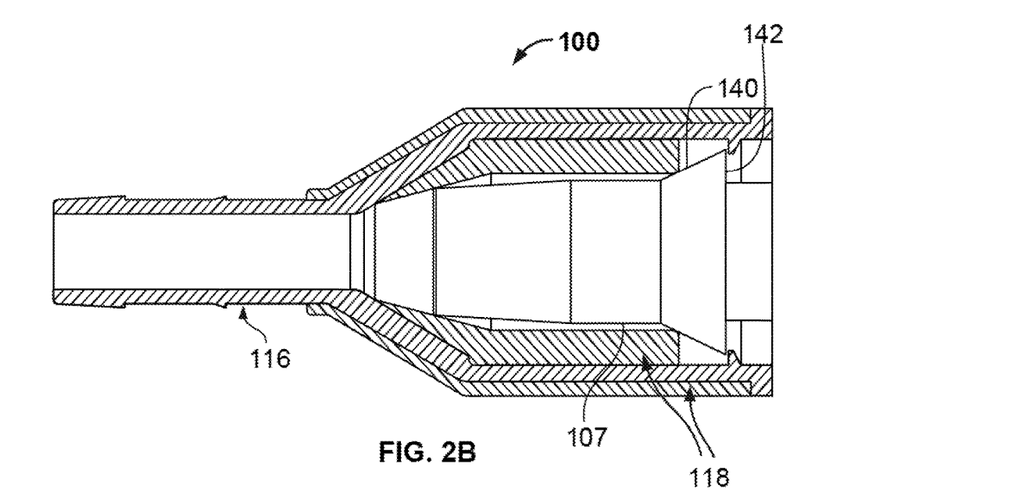

Referring to FIGS. 1, 2A and 2B, an exemplary fluid coupling device 100 includes a body 102 that has a first end portion 104 and a second end portion 106. The depicted body 102 has a bell-shaped structure in which the larger, first end portion 104 transitions to the smaller, second end portion 106. The first end portion 104 can be adapted for connecting the fluid coupling device 100 to a male barbed fitting, e.g., a male barbed fitting 107 of FIG. 2B. The second end portion 106 can include a tubular stem 108 for coupling the fluid coupling device 100 to a flexible tube (not shown). The body 102 can define a longitudinal axis (X1) and a lumen 110 that permits fluid to flow through the fluid coupling device 100. The lumen 110 at the first end portion 104 of the body 102 can be shaped and sized to receive and form a sealed connection with a male barbed fitting.

The depicted embodiment of the fluid coupling device 100 has a two-component body 102 that includes a frame 116 and a sealing material 118 disposed about at least a portion of the frame 116. The depicted frame 116 of the fluid coupling device 100 includes a first frame portion 120 that includes a ring 124 and two inwardly directed, radial locking tabs 112 for providing a quick connection to a male barbed fitting (e.g., the male barbed fitting 107 of FIG. 2B). The depicted frame 116 also includes a second frame portion 122 that forms a connecting element, e.g., the tubular stem 108. The exemplary sealing material 118 can at least partially encapsulate the frame 116 such that the sealing material 118 defines at least a portion of the lumen 110, which includes a frustoconical sealing surface 126 (see FIG. 2A) configured to form a sealed connection with the male barbed fitting. In some embodiments, the sealing material 118 can be disposed over portions of the frame 116 such that other portions the frame 116 such as, but not limited to, at least a portion of the first and second frame portions 120 and 122 are exposed. In some embodiments, only one portion of the frame 116 is exposed (not covered by the sealing material 118), e.g., the second frame portion 122.

In some embodiments, the body 102 of the fluid coupling device 100 provided herein can include a one-, two-, three-, four-, five-, six-component, or more than a six component body. The fluid coupling device 100 can be constructed, in some embodiments, as a composite body 102 made of one or more components, in which each component is composed of a different material. In some embodiments, the fluid coupling device 100 can be made of at least one component, e.g., the frame 116, that is composed of two or more different materials. Constructing one or more components of the fluid coupling device 100 with different materials offers a benefit of obtaining different chemical, mechanical, and/or physical properties desired for various components or portions of the fluid coupling device 100. For example, in some embodiments, the fluid coupling device 100 can include a frame 116 composed of a rigid material for increasing the structural integrity of the device 100 and a sealing material 118 composed of an elastomeric material for providing a desired elastic response in a compressible fluid coupling device 100.

Figure 3A:
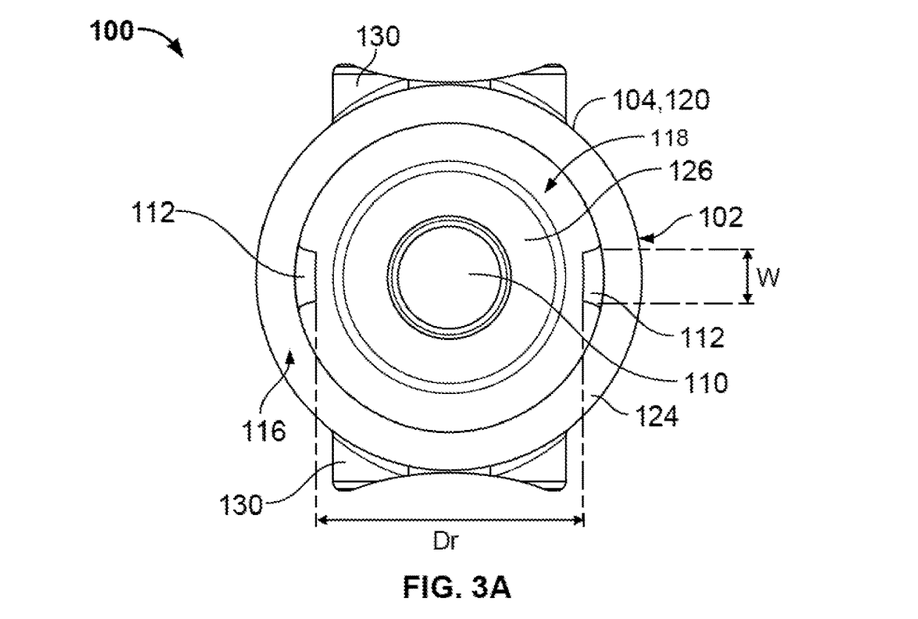
FIGS. 3A and 3B are end views of the fluid coupling device of FIG. 1 in a non-compressed and a compressed state, respectively.
Figure 3B:
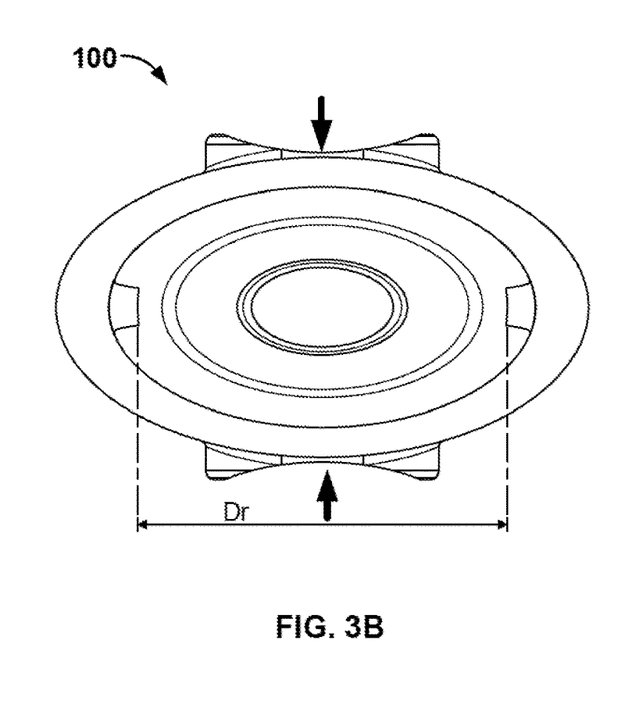

Referring to FIGS. 3A and 3B, the frame 116 and the sealing material 118 are configured to allow the fluid coupling device 100 to be quickly connected to and released from a male barbed fitting (e.g., the male barbed fitting 107 of FIG. 2B). For example, in some embodiments, a portion of the fluid coupling device 100, when compressed, can elastically deform such that its luminal cross-sectional shape changes. In various embodiments, walls (e.g., walls at the first end portion 104) of the fluid coupling device 100 can be compressed (e.g., in the direction of the depicted arrows shown in FIG. 3B) and elastically deformed for releasing a male barbed fitting. The walls of the sealing material 118 can be adapted to elastically deform and portions of the frame 116 can be deflected such that the lumen of the fluid coupling device can have a circular cross-sectional shape when the fluid coupling device is in a non-compressed state (or "free state"), as shown in FIG. 3A, and an oval cross-sectional shape when the fluid coupling device 100 is in a compressed state, as shown in FIG. 3B.

In various embodiments, the fluid coupling device 100 provided herein can be releasably coupled to a male barbed fitting (e.g., male barbed fitting 107 of FIG. 2B). In some embodiments, the fluid coupling device 100 can be releasably coupled to a male barbed fitting by alternating between two states: a non-compressed state (as shown in FIG. 3A) configured for engaging with the male barbed fitting, and a compressed state (as shown in FIG. 3B) configured for disengaging with the male barbed fitting. In the non-compressed state, the fluid coupling device 100 can be sealably coupled to the male barbed fitting 107 to create a continuous, fluid passageway between two connected system, devices and/or components. In some embodiments, when the fluid coupling device 100 is compressed, at least a portion of the frame 116 can radially deflect. In some embodiments, the fluid coupling device 100 can optionally include at least one locking feature, such as locking tabs 112, to retain a sealed connection between the male barbed fitting and the coupling device 100. For instance, as will be discussed further below, the first end portion 104 of the depicted fluid coupling device 100 can be compressed to deflect the locking tabs 112 of the frame 116 in a radially outward direction away from a male barbed fitting.

Referring back to FIGS. 1, 2A and 2B, the fluid coupling device 100 can include a sealing material 118 that encapsulates at least a portion of the frame 116. In some embodiments, the sealing material 118 can encapsulate one end, a middle portion, or fully encapsulate the entire frame 116. In various embodiments (such as the depicted embodiment), the sealing material 118 can encapsulate the frame 116 such that portions of an inner lumen wall of the fluid coupling device 100 is formed by the sealing material 118. As described further herein, portions of the sealing material 118 that form the inner lumen wall can be configured to create a sealed connection between the fluid coupling device 100 and a male barbed fitting.

The sealing material 118 can have a variety of different shapes. In some embodiments, the sealing material 118 can be bell-shaped, as shown in FIGS. 1-3. Other suitable shapes for the sealing material 118 can include, but are not limited to, a cylindrical shape, a frustoconical, or a conical shape. The sealing material 118 can be made of various materials. In some embodiments, the sealing material 118 is made of biocompatible metals, polymers and/or ceramic materials. In some embodiments, the sealing material 118 is made of an elastomeric polymer. Suitable materials for the sealing material 118 can include, but are not limited to, a natural rubbers such as polyisoprene and its derivatives, synthetic rubber such as polyvinyl chloride (PVC) and ethylene propylene diene monomer rubber (EPDM), and elastomeric thermoplastics such as a silicone.

The fluid coupling device 100 is scalable such that the fluid coupling device 100 has an outer profile that can range from about 5 millimeters (mm) to about 50 mm in diameter. In some embodiments, the outer diameter of the fluid coupling device 100 may range from about 5 mm to about 7 mm, about 7 mm to about 10 mm, about 10 mm to about 13 mm, about 13 mm to about 15 mm, about 15 mm to about 20 mm, about 20 mm to about 25 mm, about 25 mm to about 30 mm, about 30 mm to about 35 mm, about 35 mm to about 40 mm, about 40 mm to about 45 mm, about 45 mm to about 50 mm, or greater than about 50 mm.

In some embodiments, the fluid coupling device 100 can include various styles of connection configurations as well as different sizes to match a flexible tubing, or hose. For example, in some embodiments, the fluid coupling device 100 can include a connection configuration in which the body of the fluid coupling device includes a 90 degrees elbow, 45 degree elbow, sweeps, tees unions, four-way, and the like.

In some embodiments, the fluid coupling device 100 can include an outer diameter profile that includes a larger, outer diameter at the first end portion 104 that reduces to a smaller, outer diameter at the second end portion 106. In some embodiments, the larger, outer diameter can be formed by the sealing material 118 and the frame 116 while the smaller, outer diameter is formed by the frame 116 alone. The larger, outer diameter of the fluid coupling device 100 can range from about 13 mm to 50 mm, including all ranges and values therebetween. For example, in some embodiments, the larger, outer diameter may range from about 13 mm to about 15 mm, about 15 mm to about 20 mm, about 20 mm to about 25 mm, about 25 mm to about 30 mm, about 30 mm to about 35 mm, about 35 mm to about 40 mm, about 40 mm to about 45 mm, about 45 mm to about 50 mm, or greater than about 50 mm. The smaller, outer diameter of the fluid coupling device 100 can range from about 5 mm to 25 mm, including all ranges and values therebetween. For instance, in some embodiments, the smaller, outer diameter may range from about 5 mm to about 7 mm, about 7 mm to about 9 mm, about 9 mm to about 15 mm, about 15 mm to about 20 mm, about 20 mm to about 25 mm, or greater than about 25 mm.

In some embodiments, at least a portion of the fluid coupling device 100 can include a second connector adapted for coupling the fluid coupling device 100 to a second component, device or system. For example, the second end portion 106 of the fluid coupling device of FIGS. 1, 2A and 2B, includes a tubular stem 108 for coupling to flexible tubing (not shown). In some embodiments, an outer diameter of the tubular stem 108 can be sized to fit within a lumen of the flexible tubing and forms an interference fit therewith. In some embodiments, the tubular stem 108 includes a surface feature for increasing securement between the tubular stem and a luminal surface of the flexible tubing. For example, as shown in FIGS. 1-3, the outer diameter of the tubular stem 108 includes one or more barbs 128. Each barb 128 can extend about 0.1 mm to about 1.5 mm from the outer diameter of the tubular stem 108. In some embodiments, the outer diameter of the tubular stem 108 can include a roughened surface (e.g., a grit-blasted surface), or an irregular surface (e.g., a knurled surface).

The fluid coupling device 100 provided herein can include various connection configurations. For example, in some embodiments, the first end portion 104 of the fluid coupling device 100 can be configured to receive a barbed male fitting and the second end portion 106 of the fluid coupling device can include a different type of connector. As shown in FIGS. 1-3, the second end portion 106 of the depicted fluid coupling device can include a barbed tubular stem 108. In some embodiments, the second end portion 106 can include connections such as, but not limited to, a luer-lock fitting, sanitary fitting, compression fitting, taper-lock fitting, bonded connection, a pig-tail, and the like. Additionally, in some embodiments the second end portion 106 can be configured with more than one connections. For example, in some embodiments the second end portion 106 is a Y-fitting, a T-fitting, a manifold with two or more connections, and the like. In some embodiments, both the first and second end portions 104, 106 of the fluid coupling device 100 can be configured to receive barbed male fittings such that the fluid coupling device is configured like a union fitting for joining two male barbed fittings.

In various embodiments, the body 102 of the fluid coupling device 100 defines the lumen 110 extending therethrough for providing a continuous, fluid pathway. In some embodiments (such as the depicted embodiment), the lumen 110 is constructed by both the sealing material 118 and the frame 116. In some embodiments, the surface of the lumen 110 at one of the end portions is made up of entirely or primarily of the frame 116 (e.g., the lumen at the second end portion 106). In some embodiments, at one of the end portions, the surface of the lumen is entirely or primarily made up of the sealing material 118 (e.g., the lumen at the first end portion 104). In some embodiments, the lumen 110 at one end portion can be defined by a larger, inner diameter and a smaller, inner diameter at the other end portion.

As seen in FIGS. 2A and 2B, the lumen 110 of the fluid coupling device 100 can include a frustoconical sealing surface 126 (which can also be described as a first annular inner surface) adapted for sealably engaging with a male barbed fitting. The frustoconical sealing surface 126 can be constructed by the sealing material 118 in the interior of the fluid coupling device 100. The frustoconical sealing surface 126 can define an angle ($\alpha$) relative to the longitudinal axis (X1) of the body 102 that is generally complementary with a tapered end of a male barbed fitting that will be received by the fluid coupling device 100, such that a fluid-tight seal can be established therebetween. In some embodiments, the angle ($\alpha$) of the frustoconical sealing surface 126 can range from about 1 degree to about 90 degrees, or from about 15 degrees to about 40 degrees. In some embodiments, the angle ($\alpha$) of the frustoconical sealing surface 126 ranges from about 1 degree to about 5 degrees, from about 5 degrees to about 10 degrees, from about 10 degrees to about 15 degrees, from about 15 degrees to about 20 degrees, from about 20 degrees to about 25 degrees, from about 25 degrees to about 30 degrees, from about 30 degrees to about 35 degrees, from about 35 degrees to about 40 degrees, from about 40 degrees to about 40 degrees, from about 40 degrees to about 45 degrees, from about 45 degrees to about 50 degrees, from about 50 degrees to about 60 degrees, from about 60 degrees to about 70 degrees, from about 70 degrees to about 80 degrees, or from about 80 degrees to about 90 degrees. The frustoconical sealing surface 126, as shown in FIGS. 2A and 2B, can extend longitudinally within the lumen a length (L1) ranging from about 1 mm to about 10 mm. In some embodiments, the length (L1) of the frustoconical sealing surface 126 extends from about 1 mm to about 3 mm, from about 3 mm to about 5 mm, or from about 5 mm to about 10 mm. In some embodiments, the longitudinal length (L1) of the frustoconical sealing surface 126 may be less than about 1 mm or greater than about 10 mm.

The frustoconical sealing surface 126 tapers from a larger, inner diameter to a smaller, inner diameter. In some embodiments, the larger, inner diameter of the frustoconical sealing surface 126 can range from about 8 mm to about 45 mm. In some embodiments, the smaller, inner diameter of the frustoconical sealing surface 126 can range from about 5 mm to about 40 mm. The ratio of the smaller, inner diameter to the larger, inner diameter of the frustoconical sealing surface 126 can, in some embodiments, ranges from about 1:1 to about 1:10. In some embodiments, the ratio of the smaller, inner diameter to the larger, inner diameter can range from about 1:1 to about 1:2, about 1:2 to about 1:3, from about 1:3 to about 1:4, from about 1:4 to about 1:5, from about 1:5 to about 1:6, from about 1:6 to about 1:7, from about 1:7 to about 1:8, from about 1:8 to about 1:9, or from about 1:9 to about 1:10. In some embodiments, the sealing material 118 optionally includes one or more annular channels within the lumen 110 for receiving portions of the frame 116, e.g., the ring 124.

Still referring to FIGS. 2A and 2B, the lumen 110 of the fluid coupling device 100 can also include a cylindrical sealing surface 127 (which can also be described as a second annular inner surface) adapted for sealably engaging with a male barbed fitting. The cylindrical sealing surface 127 can be constructed by the sealing material 118 in the interior of the fluid coupling device 100. In some embodiments, the first cylindrical sealing surface 127 can have an inner diameter ranging from about 5 mm to about 15 mm, including all values and ranges therebetween. Suitable inner diameters for the cylindrical sealing surface can range from about 1 mm to about 3 mm, about 3 mm to about 5 mm, about 5 mm to about 7 mm, about 7 mm to about 10 mm, about 10 mm to about 13 mm, about 13 mm to about 15 mm, about 15 mm to about 20 mm, about 20 mm to about 25 mm, about 25 mm to about 30 mm, about 30 mm to about 35 mm, about 35 mm to about 40 mm, about 40 mm to about 45 mm, or greater than 45 mm. In some embodiments, the cylindrical sealing surface 127 can have a thickness ranging from about 0.25 mm to about 5 mm, including all values and ranges therebetween.

At least a portion of the cylindrical sealing surface can come into contact with an end portion or a tapered portion of a male barbed fitting, such as a tapered portion 140 of male barbed fitting 107, such that a fluid-tight seal can be established therebetween. The cylindrical sealing surface 127, as shown in FIGS. 2A and 2B, can extend longitudinally within the lumen a length (L2) ranging from about 1 mm to about 30 mm. In some embodiments, the length (L2) of the frustoconical sealing surface 126 extends from about 1 mm to about 3 mm, from about 3 mm to about 5 mm, or from about 5 mm to about 10 mm, from about 10 mm to about 15 mm, from about 15 mm to about 20 mm, or from about 20 mm to about 30 mm. In some embodiments, the longitudinal length (L2) of the cylindrical sealing surface 127 may be less than about 1 mm or greater than about 30 mm.

Still referring to FIGS. 1-3B, in some embodiments the sealing material 118 can include a pair of press pads 130. The depicted press pads 130, as shown in FIGS. 1-3B, are disk-shaped protrusions at least partially extending from of an exterior surface of the sealing material 118. Press pads 130 can have a variety of different shapes, such as a rectangular, hemispherical, oval, or square-shaped protrusion. In some embodiments, at least a portion of the press pads 130 can include a concave surface, as depicted in FIG. 3A, for facilitating manual engagement (e.g., by fingertips) with the body 102. In some embodiments, at least a portion of each press pad 130 can include a flat surface or a convex surface. In some embodiments, the press pads 130 can take the form of a depression along the exterior surface of the sealing material 118. In some embodiments, the press pads 130 may have a textured surface.

Each press pad 130 can be positioned on opposite sides of the sealing material 118 to facilitate easy manual gripping and pressurization by a user. In some embodiments, the press pads 130 are positioned to optimize the release mechanism of the fluid coupling device 100. For instance, as shown in the depicted embodiment, the press pads 130 can be circumferentially positioned where the press pads 130 generally bisect the two locking tabs 112 to maximize the amount of deflection of each locking tab 112. That is, each of the two press pads 130 can be positioned about 90 degrees from each locking tab 112. In some embodiments, the body 102 of the fluid coupling device 100 can be compressed into an unlocking, compressed state by exerting compressional forces on the press pads 130. When such compressional forces are exerted on the press pads 130, the fluid coupling device 100 is deflected such that the locking tabs 112 translate radially outward away from the axis (X1).

Figure 4:
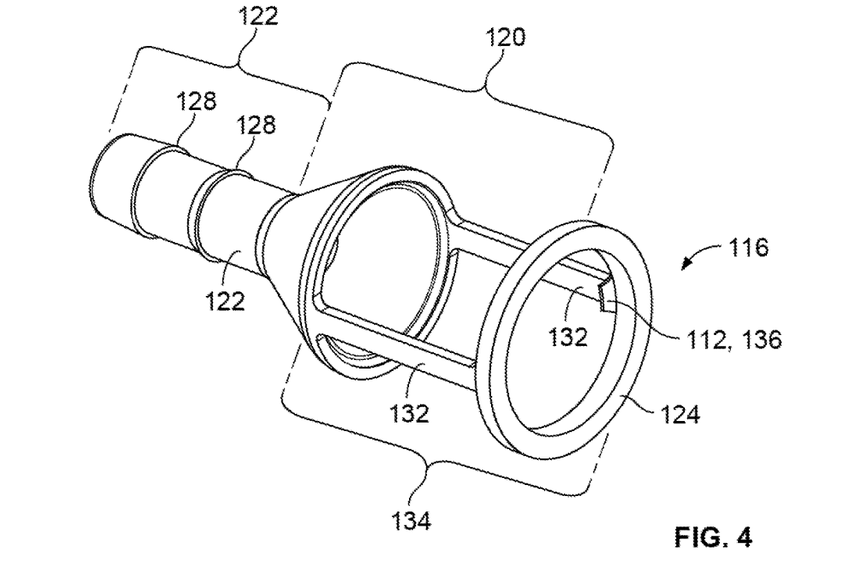
FIG. 4 is a perspective view of a frame of the fluid coupling device of FIG. 1.

Referring to FIG. 4, the frame 116 of the fluid coupling device 100 of FIG. 1 includes the first frame portion 120 and the second frame portion 122. The frame 116 can include an inner diameter that reduces from a larger diameter at the first frame portion 120 to a smaller diameter at the second frame portion 122. In some embodiments, the frame 116 can be one continuous body that extends from the first frame portion 120 to the second frame portion 122. In some embodiments, the frame 116 can include two or more separate components held in position along the body 102 by the at least partially encapsulating sealing material 118. For example, in some embodiments, the first frame portion of the frame may consist of only two tabs partially encapsulated in the sealing material.

In the depicted embodiment, the deflectable structure 134 of the frame 116 includes two axial struts 132, two locking tabs 112, and a ring 124 for facilitating disengagement of the fluid coupling device from a barbed male fitting. The deflectable structure 134 can enable the fluid coupling device 100 to be quickly released from a male barbed fitting. In some embodiments, the deflectable structure 134 can include inwardly directed, radial locking tabs 112 coupled to the ring 124. In some embodiments, each locking tab 112 can be coupled to the ring 124 and one of the axial struts 132 of the deflectable structure 134. Ovalization of the ring 124, during compression, can reversibly disengage the coupling device's locking tabs 112 from a male barbed fitting. In some embodiments, ring ovalization results in a radial distance increase between the two locking tabs 112 and deflection of the opposed, deflectable axial struts 132. Consequently, through an ovalization mechanism, the frame 116 of the fluid coupling device 100 can provide a locking mechanism for engaging with a male barbed fitting and structural rigidity to the fluid coupling device 100.

In some embodiments, the deflectable structure 134 of the frame 116 includes axial struts 132 connecting the ring 124 to the second frame portion 122 of the frame 116. When the fluid coupling device 100 is in a compressed state, each axial strut 132 can be flexible such that each strut deflects outwardly as the ring 124 becomes ovalized. In some embodiments, the frame 116 can include only one axial strut 132. In some embodiments, the frame can include more than two axial struts 132, e.g., three, four, five, or more than five axial struts. In some embodiments, each strut 132 can have a length ranging from about 10 mm to about 50 mm and a width ranging from about 1 mm to about 10 mm. The axial struts 132 can increase column strength and provide structural rigidity to the fluid coupling device 100.

The ring 124 of the frame 116 can have a circular shape when fluid coupling device 100 is in the non-compressed state and an ovular shape when the fluid coupling device 100 is in the compressed state. The ring 124 provides the fluid coupling device 100 with a desired radial strength so that the fluid coupling device 100 does not collapse due to compressional loading. The inner diameter of the ring 124 can be sized for receiving a male barbed fitting. In some embodiments, the inner diameter of the ring 124 can range from about 8 mm to about 45 mm, including all discrete values and ranges therebetween. In some embodiments, a radial width and thickness of the ring can be about 4 mm and 1 mm, respectively.

When the fluid coupling device 100 is in the compressed state (e.g., refer to FIG. 3B), the ring 124 of the frame 116 can become oval shaped, deflecting the axial struts 132 and displacing the locking tabs 112 in a radially outward direction such that a male barbed fitting can be released from the fluid coupling device 100. The frame 116 can include two locking tabs 112 positioned along an inner face of each strut 132 and adjacent to the ring 124. Each strut 132 and locking tab 112 can be positioned 180 degrees apart from one another. In some embodiments, the deflectable structure 134 of the frame 116 can include one or more than two struts 132 and/or locking tabs 112. In some embodiments, each strut 132 and/or locking tab 112 can be positioned from about 0 degrees to about 180 degrees apart from another strut 132 or locking tab 112.

Referring back to FIGS. 2A, 3A and 3B, the fluid coupling device 100 provided herein can be adapted to change the radial distance (Dr) between two or more locking tabs 112 to facilitate disengagement with a barbed male fitting. For instance, the radial distance (Dr) between the locking tabs 112 of the fluid coupling device 100 in the compressed state can be larger than the radial distance (Dr) of the fluid coupling device 100 in the non-compressed state. In some embodiments, the radial distance (Dr) between the locking tabs 112 of the fluid coupling device 100 in the compressed state can range from about 10 mm to 35 mm. The radial distance (Dr) between the locking tabs of the fluid coupling device 100 in the non-compressed state can range from about 7 mm to about 30 mm. A difference in length of the radial distance (Dr) in the compressed and the non-compressed state can range from about 0.5 mm to about 5 mm. In some embodiments, the different in length of the radial distance (Dr) in the compressed and the non-compressed state can be at least 10% of the radial distance at the non-compressed state, i.e., the free state.

Referring back to FIGS. 2A and 2B, each locking tab 112 can include a first face 136 oriented at an oblique angle relative to the longitudinal axis (X1) of the fluid coupling device 100 and a second face 138 (see FIGS. 2A and 2B) oriented at about 90 degrees relative to the longitudinal axis (X1). The angle of the first face 136 can range from about 1 degree to about 85 degrees to facilitate the passage of a male barbed fitting (e.g., male barbed fitting 107 of FIG. 2B) into the lumen of the fluid coupling device by simply pressing the male barbed fitting into the lumen. The second face 138 can be adapted to mate with a transverse surface of a barbed male fitting, e.g., transverse surface 142 of FIG. 2B, such that the male barbed fitting cannot be pulled out of the fluid coupling device 100 once the locking tabs 112 have become engaged. Each locking tab 112 can extends a radial length (R) of about 0.5 mm to about 2.0 mm. In some embodiments, each locking tab 112 can have a width (W; refer to FIG. 3) of about 1 mm to about 10 mm.

The frame 116 of the fluid coupling device 100 can be made of various materials. In some embodiments, the frame 116 may be made of biocompatible metal, polymers and/or ceramic materials. In some embodiments, the frame 116 can be made from metals such as steel, aluminum, and nitinol or their alloys. In some embodiments, the frame 116 can be made of one or more rigid plastic materials. Suitable materials for the frame 116 can include, but are not limited to, polycarbonate, polystyrene, polyethylene, polyoxymethylene (POM), and polyether ether ketone (PEEK).

Figure 5:
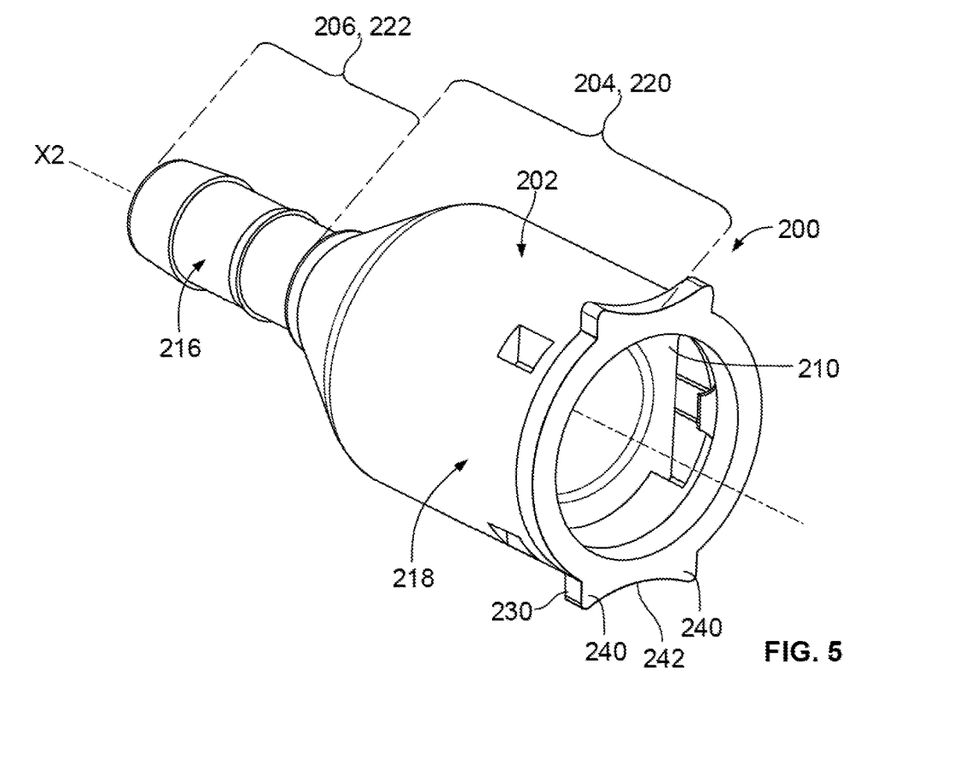
FIG. 5 is a perspective view of another exemplary fluid coupling device.

Referring to FIG. 5, another example fluid coupling device 200 includes a body 202 having a first end portion 204 and a second end portion 206. The body 202 defines a longitudinal axis (X2), and a lumen 210 that permits fluid to flow through the body. The depicted fluid coupling device 200 is similar to the fluid coupling device 100 of FIGS. 1-4 with exception of the design and location of its press elements 230.

As shown in FIG. 5, the fluid coupling device 200 has a two-piece composite body 202 that includes a sealing material 218 disposed about and partially encapsulating a frame 216. The frame 216 protrudes from the sealing material 218 at the first and second end portions 204, 206 of the body 202. A first portion 220 of the frame 216 includes a ring 124 having two press elements 230 that are positioned circumferentially opposite from one another. Each press element 230 can include two radially, outwardly extended prongs 240 with a curved depression 242 therebetween.

The fluid coupling devices 100, 200 provided herein allows for a quick connection with a male barbed fitting. For attachment, a male barbed fitting can be inserted into the first end of the fluid coupling device 100, 200. Once the male barbed fitting contacts the locking tabs 112, continual advancement of the fitting causes the axial struts 132 to initially deflect, causing the locking tab move outwardly. Further advancement of the male barbed fitting causes the locking tabs to snap back inwardly, engaging the frustoconical sealing surface of the fluid coupling device 100, 200 with the tapered profile of the male fitting. The second face of the locking tabs prevents disassembly of the fluid coupling between the two components when force is applied to withdraw the male barbed fitting from the fluid coupling device 100, 200. Specifically, the transverse edge of the male barb is mechanically stopped by the second face of the locking tab, locking the male barbed fitting in place within the fluid coupling device 100, 200.

For quick release, a fluid coupling device 100, 200 provided herein is manually deformable or hand-deformable, that is, the device provided herein can be gripped between two fingers at the press pads 130 (or press elements 230) and squeezed to release a male barbed fitting. A fluid coupling device 100, 200 provided herein can be manually deformed by compressing the device at the press pads such that the ring of the frame deflects into an oval shape. Manual deformation of a fluid coupling device 100, 200 provided herein causes the locking tabs to move in a radially outward direction and, thus, increases a gap between the locking tabs. As a result, a male barbed fitting can be withdrawn from a lumen of a fluid coupling device 100, 200 provided herein through the expanded gap formed between the locking tabs. In various embodiments, a fluid coupling device provided herein is adapted to allow a medical healthcare worker to squeeze and operate the fluid coupling device 100, 200 provided herein with a reasonable amount of force, that is, an amount of force that can be generated by a person's hand. When not being manually deformed, a fluid coupling device 100, 200 provided herein can be adapted to return to a locked state for retaining a male barbed fitting within a lumen therein. In the locked state, a fluid coupling device 100, 200 provided herein can retain a male barbed fitting such that the male barbed fitting does not fall out of or become easily dislodged from a lumen of the fluid coupling device 100, 200.

A fluid coupling device 100, 200 provided herein and components thereof can be fabricated using various manufacturing processes. In some embodiments, an over-molding process, such as injection molding, can be used to fabricate the fluid coupling device 100, 200 provided herein or components thereof. In some embodiments, suitable processes can include, but are not limited to, extrusion, compression molding, solvent casting, and combinations thereof. In some embodiments, components of the fluid coupling device 100, 200 can be mated and bonded together, e.g., by press-fitting or adhesively bonding, to form a finished device.

In some embodiments, an injection molding method can be utilized to form at least a portion of the fluid coupling device 100, 200. For example, the method can include positioning a preformed frame within a mold cavity and injecting an elastomeric material into a mold cavity such that the elastomeric material forms a sealing material over at least a portion of the frame. In some embodiments, a method of forming a fluid coupling device 100, 200 provided herein can include using a two-shot injection molding method. The two-shot injection molding method can include injecting a thermoplastic material into a mold cavity to form the frame and injecting an elastomeric material into the mold cavity such that the elastomeric material forms the sealing material over the frame.

It should be understood that one or more design features of the fluid coupling devices provided herein can be combined with other features of other fluid coupling devices provided herein. In effect, hybrid designs that combine various features from two or more of the fluid coupling device designs provided herein can be created, and are within the scope of this disclosure.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

In addition to being directed to the teachings described above and claimed below, devices and/or methods having different combinations of the features described above and claimed below are contemplated. As such, the description is also directed to other devices and/or methods having any other possible combination of the dependent features claimed below.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein. All references, publications, and patents referred to herein, including the figures and drawings included therewith, are incorporated by reference in their entirety.

What is claimed is:

1. A fluid coupling device comprising:
    a frame comprising:
        a first frame portion comprising a ring and two inwardly directed, radial locking tabs; and
        a second frame portion comprising a connecting element; and
    an elastomeric sealing material disposed about and at least partially surrounding the frame, the sealing material defining at least a portion of a lumen, the lumen comprising at least one sealing surface configured to form a sealed connection with a male barbed fitting, wherein the elastomeric sealing material defines a frustoconical sealing surface that forms at least a portion of the lumen at a first end of the first frame portion proximal the second frame portion and defining a first length, the elastomeric sealing material also defining a cylindrical sealing surface extending from the frustoconical sealing surface to a second portion of the first frame portion distal the second frame portion and defining a second length, wherein a ratio of the first length relative to the second length ranges from 1:1 to about 1:6;
    wherein the fluid coupling device, when compressed, deflects the locking tabs in a radially outward direction for releasing the male barbed fitting.

2. The fluid coupling device of claim 1, wherein the fluid coupling device has a non-compressed state configured for sealably coupling to the male barbed fitting and a compressed state configured for releasing the male barbed fitting.

3. The fluid coupling device of claim 2, wherein the ring of the frame has a circular cross-section when the fluid coupling device is in the non-compressed state and an oval cross-section when the fluid coupling device is in the compressed state.

4. The fluid coupling device of claim 1, wherein the locking tabs are located 180 degrees apart from one another.

5. The fluid coupling device of claim 1, wherein the first frame portion of the frame further comprises deflectable ring configured to increase a radial distance between the locking tabs.

6. The fluid coupling device of claim 2, wherein a radial distance between the locking tabs of the fluid coupling device in the compressed state is larger than a radial distance between the locking tabs of the fluid coupling device in the non-compressed state.

7. The fluid coupling device of claim 2, wherein a radial distance between the locking tabs of the fluid coupling device in the compressed state ranges from about 10 mm to about 35 mm.

8. The fluid coupling device of claim 2, wherein a radial distance between the locking tabs of the fluid coupling device in the non-compressed state ranges from about 7 mm to about 30 mm.

9. The fluid coupling device of claim 2, wherein a difference of a radial distance between the locking tabs of the fluid coupling device in the compressed and the non-compressed state ranges from about 0.5 mm to about 5.0 mm.

10. The fluid coupling device of claim 1, wherein the elastomeric sealing material comprises an exterior surface having two press elements.

11. The fluid coupling device of claim 10, wherein each press element is a protruding feature on the exterior surface of the sealing material.

12. The fluid coupling device of claim 10, wherein the press elements are formed on the ring and each press element comprises two radially, outwardly extended prongs and a curved depression between the two prongs.

13. The fluid coupling device of claim 1, wherein the frustoconical sealing surface is defined by an angle relative to a longitudinal axis defined by a body of the device that is complementary to a shape of a male barbed fitting.

14. The fluid coupling device of claim 1, wherein the angle of the frustoconical sealing surface relative to a longitudinal axis defined by a body of the device ranges from about 15 degrees to about 40 degrees.

15. The fluid coupling device of claim 1, wherein a ratio of a maximum inner diameter to a minimum inner diameter of the frustoconical sealing surface ranges from about 1:1 to about 1:10.

16. The fluid coupling device of claim 1, wherein the connecting element is a barbed tubular member, a luer-lock connector, or a second male barbed fitting connector.

17. The fluid coupling device of claim 1, wherein the cylindrical sealing surface at the second portion of the first frame portion distal the second frame portion ends before the locking tabs.

18. The fluid coupling device of claim 1, wherein the cylindrical sealing surface includes an inner diameter ranging from about 5 mm to about 15 mm.

19. A fluid coupling device comprising:
a body including a first fitting at a first end and a second fitting at a second end, the first fitting including a female fitting, the female fitting comprising a manually deformable frame and two inwardly directed locking tabs adapted for releasably connecting to a male barbed fluid connector, the body defining a lumen adapted for sealingly mating with the male barbed fluid connector, wherein the lumen defines a frustoconical sealing surface extending from a first end of the first fitting proximal the second fitting and defining a first length and a cylindrical sealing surface extending from the frustoconical sealing surface to a second portion of the first fitting distal the second fitting and defining a second length, wherein a ratio of the first length relative to the second length ranges from 1:1 to about 1:6.

20. The fluid coupling device of claim 19, wherein the two inwardly directed locking tabs are positioned substantially circumferentially opposite each other on the frame.

21. The fluid coupling device of claim 20, wherein the second fitting including a male fitting that comprises a barbed tube configured for insertion in a female type fluid connector.

22. A fluid coupling device comprising a frame that includes a manually deformable coupling element, the coupling element including two inwardly directed locking tabs positioned substantially circumferentially opposite each other on the frame, wherein the manually deformable coupling element defines a lumen comprising a frustoconical sealing surface that forms at least a portion of the lumen configured to form a sealed connection with a fitting, the frustoconical sealing surface extending from a first end of the frame distal the locking tabs and defining a first length and a cylindrical sealing surface extending from the frustoconical sealing surface to a second portion of the frame proximal the locking tabs and defining a second length, wherein a ratio of the first length relative to the second length ranges from 1:1 to about 1:6.

* * * * *